US006251399B1

(12) United States Patent
Diamond et al.

(10) Patent No.: US 6,251,399 B1
(45) Date of Patent: Jun. 26, 2001

(54) IMMUNO-REACTIVE PEPTIDE CTL EPITOPES OF HUMAN CYTOMEGALOVIRUS

(76) Inventors: Don Jeffrey Diamond, 415 N. Elwood Ave., Glendora, CA (US) 91741; Joanne York, 40587 174th St. East, Lancaster, CA (US) 93535

(*) Notice: Subject to any disclaimer, the term of this patent is extended or adjusted under 35 U.S.C. 154(b) by 0 days.

(21) Appl. No.: 09/534,639

(22) Filed: Mar. 27, 2000

Related U.S. Application Data

(60) Division of application No. 09/075,257, filed on May 11, 1998, now Pat. No. 6,074,645, which is a continuation-in-part of application No. 09/021,298, filed on Feb. 10, 1998, which is a continuation-in-part of application No. 08/950,064, filed on Oct. 14, 1997, now abandoned, which is a continuation-in-part of application No. 08/747,488, filed on Nov. 12, 1996, now abandoned.

(51) Int. Cl.[7] .................. A61K 39/245; A61K 39/12; A61K 38/04; A61K 35/26
(52) U.S. Cl. .................. 424/186.1; 424/204.1; 424/230.1; 424/231.1; 424/93.71; 424/93.1; 514/15; 530/328
(58) Field of Search ............... 424/186.1, 204.1, 424/230.1, 231.1, 93.1, 93.71; 514/15; 530/328

(56) References Cited

U.S. PATENT DOCUMENTS

| | | |
|---|---|---|
| 5,075,213 | 12/1991 | Pande et al. . |
| 5,405,940 | 4/1995 | Boon et al. . |
| 5,470,730 | 11/1995 | Greenberg et al. . |

FOREIGN PATENT DOCUMENTS

| | | |
|---|---|---|
| 9205794 | 4/1992 | (WO) . |
| 9606929 | 3/1996 | (WO) . |

OTHER PUBLICATIONS

Winston et al., "Ganciclovir Prophylaxis of Cytomegalovirus Infection and Disease in Allogenic Bone Marrow Transplant Recipients", Annals of Internal Medicine 118:179–184 (1993).

Riddell et al., "Therapeutic Reconstitution of Human Viral Immunity by Adoptive Transfer of Cytotoxic T Lymphocyte Clones", CurrentTopics in Microbiology and Immunology 189:9–34 (1994).

Li et al., "Recovery of HLA–Restricted Cytomegalovirus (CMV)–Specific T–Cell Responses After Allogenic Bone Marrow Transplant: Correlation with CMV Diseas and Effect of Ganciclovir Proophylaxis", Blood 83(7):1971–1979 (1994).

Johnson et al., "Induction of a Major Histocompatibility Complex I–Restricted Cytotoxic T–Lymphocyte Response to a Highly Conserved Region of Human Immunodeficiency Virus Type 1 (HIV–1) gp 120 in Seronegative Humans Immunized with a Candidate HIV–1 Vaccine", Journal of Virology 68(5):3145–3153 (1994).

Speir et al., "Potential Role of Human Cytomegalovirus and p53 Interaction in Coronary Restenosis", Science 265:391–394 (1994).

McLaughlin–Taylor et al., "Identification of the Major Late Human Cytomegalovirus Matrix Protein pp65 a Target Antigen for CD8+ Virus–Specific Cytotoxic T Lymphocytes", Journal of Medical Virology 43:1 110 (1994).

Vitiello et al., "Development of a Lipopeptide–based Therapeutic Vaccine to Treat Chronic HBV Infection", J. Clin. Invest. 95:341–349 (1995).

Walter et al., "Reconstitution of Cellular Immunity Cytomegalovirus in Recipients of Allogeneic Bone Marrow by Transfer of T–Cell Clones from the Donor", The New England Journal of Medicine 333(16):1038–1044 (1995).

Drijfhout et al., "Detailed Motifs for Peptide Binding to HLA–A*0201 Derived from Large Random Sets of Peptides Using a Cellular Binding Assay", Human Immunology 43:1–12 (1995).

D'Amaro et al., "A Computer Program for Predicting Possible Cytotoxic T Lymphocyte Epitopes Based on HLA Class I Peptide–Binding Motifs", Human Immunology 43:13–18 (1995).

Rasmussen, "Immune Response to Human Cytomegalovirus Infection", Current Topics in Microbiology and Immunology 154:222–254 (1990).

Zhou et al., "Association Between Prior Cytomegalovirus Infection and the Risk of Restenosis After Coronary Atherectomy", The New England Journal of Medicine 335(9);624–630 (1996).

Moss, "Vaccina Virus Vectors", Construction of Recombinant Viruses, Chapter 15, pp. 345–362.

Pande et al., "Direct DNA Immunization of Mice with Plasmid DNA Encoding the Tegument Protein pp65 (ppUL83) of Human Cytomegalovirus Induces High Levels of Circulating Antibody to the Encoded Protein" Scand J Infect Dis Suppl 99, (Sweden) 1995 p 117–120.

(List continued on next page.)

Primary Examiner—Ali R. Salimi
(74) Attorney, Agent, or Firm—Rothwell, Figg, Ernst & Manbeck

(57) ABSTRACT

The invention provides a plurality of peptides (and immunologically functional variants thereof) which are immunogenic epitopes recognized by CD8+ class I MHC restricted cytotoxic T-lymphocytes of patients harboring latent cytomegalovirus (HCMV) infection. The peptides are capable of activating CTLs and CTLp's in the absence of active viral replication, and thus are useful for eliciting a cellular immune response against HCMV by normal and immunodeficient subjects. Polypeptide and lipopeptide vaccines, with and without adjuvants, also are disclosed.

9 Claims, 1 Drawing Sheet

OTHER PUBLICATIONS

Khattab, B.A. et al., "Three T–Cell Epitopes Within the C–Terminal 265 Amino Acids of the Matrix Protein pp65 of Human Cytomegalovirus Recognized by Human Lymphocytes," Journal of Medical Virology, 52:68–76 (1997).

Ogg, G.H. et al., "HLA–peptide tetrameric complexes," Immunology, 10:393–396 (1998).

Pande, H. et al., "Human Cytomegalovirus Strain Towne pp65 Gene: Nucleotide Sequence and Expression in *Escherichia coli*," Virology 182:220–228 (1991).

Parker, K. et al., "Scheme for Ranking Potential HLA–A2 Binding Peptides Based on Independent Binding of Individual Peptide Side–Chains," Journal of Immunology 152:163–175 (1994).

Wills, M.R. et al., "The human CTL response to Cytomegalovirus is dominated by structural protein," J. Virology 70:(11):7569–7579 (1996).

Tsunoda T. et al., "Seriologically identically HLA B35 alleles which do not cross–present minimal cytotoxic epitopes to CD8+CTL," J. Cell Biochem. vol. Suppl. 0(19A):298, Abstr. No. J2–218 (1995).

Diamond, D.J. et al., "In vivo priming of virus–specific cytotoxic T lymphocytes with synthetic lipopeptide vaccine," Nature 342:561–564 (1989).

Gonczol E. et al., "Preclinical evaluation of an ALVAC (canarypox)–human cytomegalovirus glycoprotein B vaccine candidate," Vaccine 13(12):1080–1085 (1995).

Rammensee et al., Immunogenetics 41(4):178–228 (1995).

Livingston et al., J. Immunol. 159:1383–1392 (1997).

Quinnan et al., "HLA–Restricted T–Lymphocyte and Non––T–Lymphocyte Cytotoxic Responses Correlate with Recovery from Cytomegalovirus Infection in Bone–Marrow–Transplant Recipients", The New England Journal of Medicine, Cytomegalovirus Infection 307(1): 7–13 (1982).

Borysiewicz et al., "Human Cytomegalovirus–Specific Cytotoxic T Lymphocytes: Requirements for in vitro Generation and Specificity", Eur. J. Immunol. 13:804–809 (1983).

Clark et al., "Isolation and Partial Chemical Characterization of a 64,000–Dalton Glycoprotein of Human Cytomegalovirus", Journal of Virology, Notes 49(1):279–282 (1984).

Forman et al., "A 64,000 Dalton Matrix Protein of Human Cytomegalovirus Induces In Vitro Immune Responses Similar to Those of Whole Viral Antigen", The Journal of Immunology, 134(5):3391–3395 (1985).

Meyers et al., "Risk Factors for Cytomegalovirus Infection After Human Marrow Transplantation", The Journal of Infectious Diseases 153(3):478–488 (1986).

Miller et al., "Retrovirus–Mediated Gene Transfer into Human Skin Fibroblasts", Mar. 1988 Meeting at Cold Spring Harbor.

Borysiewicz et al., "Relative Frequency of Stage–Specific CTL Recognizing the 72–kD Immediate Early Protein and Glycoprotein B Expressed by Recombinant Vaccinia Viruses", J. Exp. Med. 168:919–931 (1988).

Miller et al., "Design of Retrovirus Vectors for Transfer and Expression of the Human β–Globin Gene", Journal of Virology 62(11):4337–4345 (1988).

Townsend et al., "Recognition of Influenza Virus Proteins by Cytotoxic T Lymphocytes", Phil. Trans. R. Soc. Lond. B 323:527–533 (1989).

Gelinas et al., "Regulated Expression of the Human β–Globin Gene After Retroviral Transfer into Murine and Human Hematopoietic Cells", Hemoglobin Switching, Part B: Cellular and Molecular Mechanisms, pp. 235–249 (1989).

Pande et al., "Structural Analysis of a 64–kDa Major Structural Protein of Human Cytomegalovirus (Towne): Identification of Phosphorylation Site and Comparison to pp65 of HCMV (AD169)", Virology 178:6–14 (1990).

Falk et al., "Allele–Specific Motifs Revealed by Sequencing of Self–Peptides Eluted from MHC Molecules", Nature 351:290–296 (1991).

Schmidt et al., "A Randomized, Controlled Trial of Prophylactic Ganciclovir for Cytomegalovirus Pulmonary Infection in Recipients of Allogeneic Bone Marrow Transplants", The New England Journal of Medicine, 324(15):1005–1011 (1991).

Del Val et al., "Efficient Processing of an Antigenic Sequence for Presentation by MHC Class I Molecules Depends on Its Neighboring Residues in the Protein", Cell 68:1145–1153 (1991).

Penna et al., "Cytotoxic T Lymphocytes Recognize an HLA–A2–Restricted Epitope Within the Hepatitis B Virus Nucleocapsid Antigen", J. Exp. Med. 174:1565–1570 (1991).

Goodrich et al., "Early Treatment with Ganciclovir to Prevent Cytomegalovirus Disease After Allogeneic Bone Marrow Transplantation", The New England Journal of Medicine 325(23):1601–1607 (1991).

Reusser et al., "Cytotoxic T–Lymphocyte Response to Cytomegalovirus After Human Allogeneic Bone Marrow Transplantation: Pattern of Recovery and Correlation With Cytomegalovirus Infection and Disease," Blood 78(5):1373–1380 (1981).

Riddell et al., "Restoration of Viral Immunity in Immunodeficient Humans by the Adoptive Transfer of T Clones", Science 257:238–241 (1992).

Missale et al., "HLA–A31 and HLA–Aw68–Restricted Cytotoxic T Cell Responses to a Single Hepatitis B Virus Nucleocapsid Epitope During Acute Viral Hepatitis", J. Exp. Med. 177:751–762 (1993).

Gilbert et al., "Selective Interference with Class I Major Histocompatibility Complex Presentation of the Major Immediate–Early Protein Following Infection with Human Cytomegalovirus", Journal of Virology 67(6):3461–3469 (1993).

Bertoletti et al., "Definition of a Minimal Optimal Cytotoxic T–Cell Epitope within the Hepatitis B Virus Nucleocapsid Protein", Journal of Virology 67(4):2376–2380 (1993).

Kast et al., "Human Leukocyte Antigen–A2.1 Restricted Candidate Cytotoxic T Lymphocyte Epitopes of Human Papillomavirus Type 16 E6 and E7 Proteins Identified by Using the Processing–Defective Human Cell Line T2", Journal of Immunotherapy 14:115–120 (1993).

Ralston et al., "Characterization of Hepatitis C Virus Envelope Glycoprotein Complexes Expressed by Recombinant Vaccinia Viruses", Journal of Virology 67(11):6753–6761 (1993).

Goodrich et al., "Ganciclovir Prophylaxis To Prevent Cytomegalovirus Disease after Allogeneic Marrow Transplant", Annals of Internal Medicine 118:173–178 (1993).

SEQUENCE LISTING

```
<160> NUMBER OF SEQ ID NOS: 20

<210> SEQ ID NO: 1
<211> LENGTH: 9
<212> TYPE: PRT
<213> ORGANISM: Human Cytomegalovirus

<400> SEQUENCE: 1

Asn Leu Val Pro Met Val Ala Thr Val
  1               5

<210> SEQ ID NO: 2
<211> LENGTH: 9
<212> TYPE: PRT
<213> ORGANISM: Artificial Sequence
<220> FEATURE:
<221> NAME/KEY: VARIANT
<222> LOCATION: (2)
<223> OTHER INFORMATION: Xaa = Leu, Ile, Met, Thr or Val
<220> FEATURE:
<221> NAME/KEY: VARIANT
<222> LOCATION: (9)
<223> OTHER INFORMATION: Xaa = Val, Ala, Cys, Ile, Leu or Thr
<220> FEATURE:
<223> OTHER INFORMATION: Description of Artificial Sequence: Human
      Cytomegalovirus Epitope Variant

<400> SEQUENCE: 2

Asn Xaa Val Pro Met Val Ala Thr Xaa
  1               5

<210> SEQ ID NO: 3
<211> LENGTH: 11
<212> TYPE: PRT
<213> ORGANISM: Human Cytomegalovirus

<400> SEQUENCE: 3

Tyr Ser Glu His Pro Thr Phe Thr Ser Gln Tyr
  1               5                  10

<210> SEQ ID NO: 4
<211> LENGTH: 11
<212> TYPE: PRT
<213> ORGANISM: Artificial Sequence
<220> FEATURE:
<221> NAME/KEY: VARIANT
<222> LOCATION: (2)
<223> OTHER INFORMATION: Xaa = Ser, Thr or Leu
<220> FEATURE:
<223> OTHER INFORMATION: Description of Artificial Sequence: Human
      Cytomegalovirus Epitope Variant

<400> SEQUENCE: 4

Tyr Xaa Glu His Pro Thr Phe Thr Ser Gln Tyr
```

```
                1               5                  10

<210> SEQ ID NO: 5
<211> LENGTH: 11
<212> TYPE: PRT
<213> ORGANISM: Human Cytomegalovirus

<400> SEQUENCE: 5

Phe Val Phe Pro Thr Lys Asp Val Ala Leu Arg
 1               5                  10

<210> SEQ ID NO: 6
<211> LENGTH: 11
<212> TYPE: PRT
<213> ORGANISM: Artificial Sequence
<220> FEATURE:
<221> NAME/KEY: VARIANT
<222> LOCATION: (2)
<223> OTHER INFORMATION: Xaa = Val or Thr
<220> FEATURE:
<221> NAME/KEY: VARIANT
<222> LOCATION: (11)
<223> OTHER INFORMATION: Xaa = Leu, Arg or Lys
<220> FEATURE:
<223> OTHER INFORMATION: Description of Artificial Sequence: Human
      Cytomegalovirus Epitope Variant

<400> SEQUENCE: 6

Phe Xaa Phe Pro Thr Lys Asp Val Ala Leu Xaa
 1               5                  10

<210> SEQ ID NO: 7
<211> LENGTH: 10
<212> TYPE: PRT
<213> ORGANISM: Human Cytomegalovirus

<400> SEQUENCE: 7

Thr Pro Arg Val Thr Gly Gly Gly Ala Met
 1               5                  10

<210> SEQ ID NO: 8
<211> LENGTH: 10
<212> TYPE: PRT
<213> ORGANISM: Artificial Sequence
<220> FEATURE:
<221> NAME/KEY: VARIANT
<222> LOCATION: (10)
<223> OTHER INFORMATION: Xaa = Leu, Phe or Met
<220> FEATURE:
<223> OTHER INFORMATION: Description of Artificial Sequence: Human
      Cytomegalovirus Epitope Variant

<400> SEQUENCE: 8

Thr Pro Arg Val Thr Gly Gly Gly Ala Xaa
 1               5                  10

<210> SEQ ID NO: 9
<211> LENGTH: 8
<212> TYPE: PRT
<213> ORGANISM: Human Cytomegalovirus

<400> SEQUENCE: 9

Phe Pro Thr Lys Asp Val Ala Leu
 1               5

<210> SEQ ID NO: 10
<211> LENGTH: 10
<212> TYPE: PRT
```

```
<213> ORGANISM: Human Cytomegalovirus

<400> SEQUENCE: 10

Ile Leu Ala Arg Asn Leu Val Pro Met Val
 1               5                  10

<210> SEQ ID NO: 11
<211> LENGTH: 9
<212> TYPE: PRT
<213> ORGANISM: Human Cytomegalovirus

<400> SEQUENCE: 11

Glu Leu Glu Gly Val Trp Gln Pro Ala
 1               5

<210> SEQ ID NO: 12
<211> LENGTH: 9
<212> TYPE: PRT
<213> ORGANISM: Human Cytomegalovirus

<400> SEQUENCE: 12

Arg Ile Phe Ala Glu Leu Glu Gly Val
 1               5

<210> SEQ ID NO: 13
<211> LENGTH: 29
<212> TYPE: PRT
<213> ORGANISM: Artificial Sequence
<220> FEATURE:
<223> OTHER INFORMATION: Description of Artificial Sequence: Human
      Cytomegalovirus Vaccine

<400> SEQUENCE: 13

Lys Ser Ser Gln Tyr Ile Lys Ala Asn Ser Lys Phe Ile Gly Ile Thr
 1               5                  10                  15

Glu Ala Ala Ala Asn Leu Val Pro Met Val Ala Thr Val
            20                  25

<210> SEQ ID NO: 14
<211> LENGTH: 29
<212> TYPE: PRT
<213> ORGANISM: Artificial Sequence
<220> FEATURE:
<223> OTHER INFORMATION: Description of Artificial Sequence: Human
      Cytomegalovirus Vaccine

<400> SEQUENCE: 14

Cys Ser Ser Gln Tyr Ile Lys Ala Asn Ser Lys Phe Ile Gly Ile Thr
 1               5                  10                  15

Glu Ala Ala Ala Asn Leu Val Pro Met Val Ala Thr Val
            20                  25

<210> SEQ ID NO: 15
<211> LENGTH: 28
<212> TYPE: PRT
<213> ORGANISM: Artificial Sequence
<220> FEATURE:
<221> NAME/KEY: VARIANT
<222> LOCATION: (6)
<223> OTHER INFORMATION: Xaa = cyclohexylalanine or phenylalanine
<220> FEATURE:
<223> OTHER INFORMATION: Description of Artificial Sequence: Human
      Cytomegalovirus Vaccine

<400> SEQUENCE: 15

Lys Ser Ser Ala Lys Xaa Val Ala Ala Trp Thr Leu Lys Ala Ala Ala
```

```
                1               5              10              15
Gly Gly Gly Asn Leu Val Pro Met Val Ala Thr Val
                    20                  25

<210> SEQ ID NO: 16
<211> LENGTH: 28
<212> TYPE: PRT
<213> ORGANISM: Artificial Sequence
<220> FEATURE:
<221> NAME/KEY: VARIANT
<222> LOCATION: (6)
<223> OTHER INFORMATION: Xaa = cyclohexylalanine or phenylalanine
<220> FEATURE:
<223> OTHER INFORMATION: Description of Artificial Sequence: Human
      Cytomegalovirus Vaccine

<400> SEQUENCE: 16

Cys Ser Ser Ala Lys Xaa Val Ala Ala Trp Thr Leu Lys Ala Ala Ala
  1               5                  10                  15
Gly Gly Gly Asn Leu Val Pro Met Val Ala Thr Val
                    20                  25

<210> SEQ ID NO: 17
<211> LENGTH: 25
<212> TYPE: PRT
<213> ORGANISM: Artificial Sequence
<220> FEATURE:
<221> NAME/KEY: VARIANT
<222> LOCATION: (6)
<223> OTHER INFORMATION: Xaa = cyclohexylalanine or phenylalanine
<220> FEATURE:
<223> OTHER INFORMATION: Description of Artificial Sequence: Human
      Cyctomegalovirus Vaccine

<400> SEQUENCE: 17

Lys Ser Ser Ala Lys Xaa Val Ala Ala Trp Thr Leu Lys Ala Ala Ala
  1               5                  10                  15
Asn Leu Val Pro Met Val Ala Thr Val
                20                  25

<210> SEQ ID NO: 18
<211> LENGTH: 29
<212> TYPE: PRT
<213> ORGANISM: Artificial Sequence
<220> FEATURE:
<223> OTHER INFORMATION: Description of Artificial Sequence: Human
      Cytomegalovirus Vaccine

<400> SEQUENCE: 18

Lys Ser Ser Ile Ser Gln Ala Val His Ala Ala His Ala Glu Ile Asn
  1               5                  10                  15
Glu Ala Ala Ala Asn Leu Val Pro Met Val Ala Thr Val
                    20                  25

<210> SEQ ID NO: 19
<211> LENGTH: 11
<212> TYPE: PRT
<213> ORGANISM: Human Cytomegalovirus

<400> SEQUENCE: 19

Arg Pro His Glu Arg Asn Gly Phe Thr Val Leu
  1               5                  10

<210> SEQ ID NO: 20
<211> LENGTH: 12
<212> TYPE: PRT
```

```
<213> ORGANISM: Human Cytomegalovirus

<400> SEQUENCE: 20

Ser Val Leu Gly Pro Ile Ser Gly His Val Leu Lys
  1               5                  10
```

IMMUNO-REACTIVE PEPTIDE CTL EPITOPES OF HUMAN CYTOMEGALOVIRUS

This application is a divisional of 09/075,257, filed May 11, 1998, now U.S. Pat. No. 6,074,645 which is a continuation-in-part of co-pending application Ser. No. 09/021,298, filed Feb. 10, 1998, which is a continuation-in-part of application Ser. No. 08/950,064, filed Oct. 14, 1997, now abandoned which is a continuation-in-part of application Ser. No. 08/747,488, filed Nov. 12, 1996, now abandoned.

STATEMENT REGARDING FEDERALLY SPONSORED RESEARCH

This invention was made with government support in the form of grant no. CA30206 from the United States Department of Health and Human Services, National Cancer Institute. The government may have certain rights in the invention.

BACKGROUND OF THE INVENTION

1. Technical Field

This invention relates to human cytomegalovirus (HCMV), and in particular to peptide fragments from a single subunit protein that function as T-cell epitopes of HCMV in human beings. The peptide fragments are capable of directing human cytotoxic T lymphocytes (CTL) to recognize and lyse human cells infected with HCMV. The peptide fragments can independently direct HCMV-specific CTL to lyse cells incubated with the peptide and which express HLA A, B or C genes.

2. Description of the Background Art

The HCMV genome is relatively large (about 235 k base pairs) and has the capacity to encode more than two hundred proteins. HCMV is composed of a nuclear complex of nucleic acid (double-stranded DNA) surrounded by capsid proteins having structural or enzymatic functions, and an external glycopeptide- and glycolipid-containing membrane envelope. HCMV is a member of the herpes virus family and has been associated with a number of clinical syndromes.

HCMV infection is relatively common and is usually self-limiting in the healthy, immunocompetent child or adult (L. Rasmussen, Curr. Top. Microbiol. Immunol. 154:221–254, 1990). Approximately ten percent (10%) of all newborn infants carry HCMV and the virus can cause severe congenital disease in the fetus or infant. Some of these newborn infants suffer congenital birth defects. Other newborn infants carry cytomegalovirus for some time before they actually show symptoms of the disease. For example, HCMV is a common cause of mental retardation in children who acquire the infection in utero from mothers carrying an active infection.

Several studies have begun to question whether persistent and apparently asymptomatic HCMV infection in an otherwise healthy adult poses health risks in certain individuals. For example, individuals who have undergone coronary angioplasty sometimes subsequently develop restenosis as a result of arterial remodeling. In one study, about one third of such patients with restenosis had detectable HCMV DNA in their arterial lesions (E. Speir et al., Science 265:391–394 (1994)), whereas in another study CMV seropositive patients were five times more likely to develop restenosis than their seronegative counterparts (Y. F. Zhou et al., New England J. Med. 335:624–630 (1996)). These studies suggest that decreasing the number of HCMV infected host cells can benefit certain individuals.

HCMV also has been associated with morbidity and mortality in immuno-compromised patients. HCMV is an important consideration in the treatment of patients suffering from Acquired Immunodeficiency Syndrome (AIDS). The defining complication is retinitis, which, if left untreated, can lead to blindness. Historically, CMV disease has been one of the more devastating of the opportunistic infections (OI) that beset HIV-1-infected individuals whose $CD4^+$ T cell level diminishes below $100/mm^3$. Other disease manifestations of CMV viremia also appear as the $CD4^+$ T cell counts drops below $100/mm^3$, including encephalitis, enteritis and pneumonia. At autopsy there is multi-organ involvement of CMV disease in the preponderance of AIDS patients who had severe CMV retinitis.

Patients infected with HCMV often suffer impairment of some of their vital organs, including the salivary glands, brain, kidney, liver and lungs, as a result of the effects of the disease. Furthermore, HCMV is associated with a wide spectrum of classical syndromes including mononucleosis and interstitial pneumonia. HCMV also has an oncogenic potential and a possible association with certain types of malignancies including Kaposi's sarcoma.

HCMV can cause opportunistic infections resulting in a variety of complications in, for example, immunosuppressed organ transplant patients. Prior to the use of antiviral chemotherapy, HCMV infection had been responsible for a substantial proportion of post-bone marrow transplantation (BMT) complications (J. Meyers et al., J. Infect Dis. 153:478–488 (1986)). The advent of drugs such as ganciclovir with substantial anti-CMV activity dramatically reduced complications associated with post-BMT CMV infections (G. Schmidt et al. New England J. Med. 324:1005–1011 (1991) and J. M. Goodrich et al., New England J. Med. 325:1601–1607 (1991)). Ganciclovir is most effective when administered prophylactically before diagnosis of HCMV infection. This approach has several negative aspects including a higher proportion of recipients becoming neutropenic (one third) and increased numbers of concomitant fatal bacterial and fungal diseases (J. M. Goodrich et al., Ann. Intern. Med. 118:173–178 (1993)). An alternative approach in which ganciclovir was given when HCMV antigens or DNA are first detected by culture methods provided no survival advantage compared to prophylaxis or treatment post-disease for all patients (D. J. Winston et al., Ann. Intern. Med. 118:179–184 (1993)). Finally, because of the acute nature of the side-effects, there is a need for increased hospitalization and growth factor administration to treated patients which, coupled with the cost of ganciclovir prophylaxis, increases the cost of BMT aftercare.

Because human cytomegalovirus is relatively common, yet is associated with extremely serious health conditions, a considerable effort has been made to study the biology of the virus with the aims of improving diagnosis of the disease as well as developing preventative and therapeutic strategies.

The mounting of a $CD8^+$ TL response is believed to be an important mammalian host response to certain acute viral infections. The observations that HCMV infection is widespread and persistent, and may be reactivated and become clinically evident in the immunosuppressed patient, have suggested that virus-specific T-cells, including HCMV-specific CTL, play an important role in the control of persistent infection and the recovery from CMV disease.

In humans, protection from the development of CMV disease in immunosuppressed BMT recipients correlates with the recovery of measurable CD8+ CMV-specific class I MHC-restricted T cell responses (Quinnan et al., *N. Eng. J. Med.* 307:7–13 (1982); Reusser et al., *Blood* 78:1373–1380 (1991)). These observations led investigators to carry out clinical trials in which donor-derived CMV-specific CD8+ CTL were infused into BMT recipients as an alternative to ganciclovir prophylaxis and therapy (S. R. Riddell et al., *Science* 257:238–241 (1992)). The transfer of CD8+ CTL clones to allogeneic bone marrow transplant recipients results in detectable CTL-based CMV immunity, and statistically significant diminution of CMV disease after BMT (E. A. Walter et al., *N. Eng. J. Med.* 333:1038–1044 (1995)).

Although successful in application, this approach has the disadvantage that it requires a sophisticated laboratory setup (which is also highly labor-intensive and costly) to derive the HCMV-specific CTL in vitro to be reinfused into a patient. A desirable alternative would be to deliver a vaccine derived from HCMV that would impart immunity to a BMT recipient, a solid organ recipient, a heart patient, an AIDS patient or a woman of child-bearing years, without the need for ex vivo expansion of HCMV-specific CTL. To develop such a vaccine, the viral proteins which cause the host to recognize HCMV in a protective manner must be identified, so that their amino acid sequence information can be determined. No such vaccine presently is available, however.

The viral life cycle provides insight as to the most effective time frame for targeting a vaccine to maximally disrupt virus production and spread. Following HCMV entry into the host cell and uncoating, the viral genome is expressed sequentially via immediate early (0–2 hour), early (2–24 hour) and late (>24 hour) viral proteins. However, certain viral structural proteins such as pp65 are chaperoned into the cell because of their existence in large quantity in the viral particle. Much attention has focused upon structural virion proteins as potential immunodominant target antigens for HCMV-specific CTL responses.

One viral structural protein, pp65, has been identified as a target antigen for CMV-specific class I MHC restricted CTL derived from the peripheral blood of most asymptomatic CMV seropositive individuals (E. Mclaughlin-Taylor et al., *J. Med. Virol.* 43:103–110 (1994)). Importantly, CD8+ class I MHC restricted CTL specific for pp65 will recognize autologous HCMV-infected cells without the requirement for viral gene expression, presumably as a result of processing of the internal depot of pp65 that is transferred into the cell during infection (M. J. Gilbert et al., *J. Virology* 67:3461–3469 (1993)). CTL against pp65 or pp150 (another matrix protein that is recognized frequently) are able to recognize and lyse HCMV-infected cells in vitro within an hour of infection in the absence of viral gene expression (S. R. Riddell and P. D. Greenberg, *Curr. Top. Microbiol. Immunol.* 189:9–34 (1994)). Thus, these CTL may represent an important effector cell for limiting HCMV reactivation and progression to CMV disease, and such a cellular immune response in both immunocompromised and normal individuals would be extremely important (C.-R. Li et al., *Blood* 83:1971–1979 (1994)). Alternatively, CTL recognizing envelope proteins are not a substitute for pp65 and pp150 CTL because they are rarely found, arising late in infection and they are poor lytic effectors because of the down-regulation of the required Class I MHC molecules (M. J. Gilbert et al., *J. Virology* 67:3461–3469 (1993)). Finally, the HCMV major protein IE, produced abundantly early after infection, is specifically inhibited from being a stimulator of CD8+ CTL by a CMV-dependent blockade of its presentation (M. J. Gilbert et al., *Nature [London]* 383:720–722, 1996). Therefore, vaccines stimulating immunity against pp65 or pp150 would be the preferred mechanism for eliciting protective immunity against CMV infection.

It has been established that individual MHC Class I molecules preferentially bind peptides of a given motif and that the amino acid sequence of specific positions of the motif are invariant, allowing a given peptide to bind to MHC Class I molecules with high affinity. These are referred to as "anchor positions" (K. Falk et al., *Nature* 351:290–296 (1991)). Later studies have suggested that amino acid positions other than the anchor positions also contribute to the specificity of peptide binding to MHC Class I molecules. Additionally, residues at positions within the CTL epitope which do not interact with MHC may interact with T cells, presumably by binding the T Cell receptor (TCR). The binding of peptide amino acid residues to MHC or TCR structures is independently governed, so that substitution of TCR binding amino acid residues in many cases will not interfere with binding to the MHC molecule on the surface of an antigen presenting cell.

Edman degradation followed by N-terminal sequence analysis has been used to sequence the peptide mixture which is bound to the MHC class I peptide binding groove. In most cases the length of these peptides is between 9 and 11 amino acids. Mass spectrometry of HPLC separated peptide mixtures can elucidate the primary sequence of individual peptides. Peptide fragments which bind to MHC identified in this manner are referred to as "naturally processed epitopes." Alternatively, one can predict which peptides of a given length, between 9–11 amino acids, will optimally bind to individual HLA Class I alleles based on their conformity to a motif (K. Falk et al., *Nature* 351:290–296 (1991)). One such motif has been established for HLA A*0201. Positions 2 and 9 of a nonapeptide are anchor residues for HLA A*0201, with minor contributions to binding from positions 1, 4, 3, 5, 6, 7, 8 in decreasing order of importance to binding strength (J. W. Drijfhout et al., *Human Immunology* 43:1–12 (1995)). Similar motifs have been established for decamers and undecamers for HLA A*0201. Correspondingly, unique amino acid motifs have been established for a subset of other HLA A and B alleles to predict binding peptides between 8–11 amino acids (H. G. Rammensee et al., *Immunogenetics* 41 (4):178–228 (1995)).

It is recognized that CTL are an important mechanism by which a mammalian organism defends itself against infection by viruses and possibly cancer. A processed form of, e.g., a viral protein minimal cytotoxic epitope (MCE) in combination with MHC Class I molecules is recognized by T cells, such as CD8+ CTL. Functional studies of viral and tumor-specific T cells have confirmed that an MCE of 8–12 amino acids can prime an antigen presenting cell (APC) to be lysed by CD8+ CTL, as long as the APC expresses on the cell surface the correct MHC molecule that will bind the peptide.

It has been shown that the route of entry of a protein into the cell determines whether it will be processed as an antigen bound to either MHC Class I or II molecules. The endogenous or Class I pathway of protein degradation is often used by infectious viruses when they are present within cells. Viral nucleoproteins which may never reach the cell surface as full length molecules are still processed within the cell, and degraded portions are transported to the surface via MHC Class I molecules. Viral envelope glycoproteins, merely because they are cell surface molecules, do not obligatorily induce CTL recognition. Rather, it has been found that viral nucleoproteins, predominantly in the form of processed epitopes are the target antigens recognized by CD8+ CTL (A. Townsend et al., *Philos. Trans. R. Soc. Lond.(Biol)*. 323:527–533 (1989)).

As it has become apparent that antigens entering the cell through exogenous pathways (pinocytosis, etc.) are not typically processed and presented by Class I MHC molecules, methods to introduce proteins directly into the cytoplasm have become the focus of vaccine developers. An approach that had gained favor was to use recombinant vaccinia viruses to infect cells, delivering a large amount of intracellular antigen. The enthusiasm for using vaccinia viruses as vaccines has diminished, however, because these viruses have the potential to cause disease in immunosuppressed people, such as BMT recipients. Another approach to vaccination is to mix an antigenic protein with an adjuvant and introduce the mixture under the skin by subcutaneous injection.

Yet another potential approach to immunization to elicit CTL is to use the MCE defined for a viral antigen in the context of a particular MHC restriction element to boost a CTL memory response to a virus. The ability of an MCE to provide protective immunity to challenge by a lethal dose of an infectious virus has been discussed in the literature. Vaccine developers have developed increasing interest in utilizing the MCE as the vaccine because it is capable of binding to MHC Class I molecules through external binding of the cell surface molecules without the need for internalization or processing. The MCE has been most effective as an immunogen when synthesized as a lipidated peptide together with a helper CD4 epitope (A. Vitiello et al., *J. Clin. Invest*. 95:341–349 (1995) and B. Livingston et al., *J. Immunol*. 159:1383–1392, 1997). Other modifications of the bivalent vaccine include inclusion of a signal sequence (KDEL) for endoplasmic reticulum retention and targeting to attain maximum activity. There is also evidence in the literature that an MCE presented by particular types of APC (e.g. dendritic cells) may cause a primary immune response to occur in the absence of viral infection or prior contact with the virus or tumor cell.

Accordingly, in spite of significant efforts towards identifying the HCMV proteins that are recognized by CTLs, as well as the specific identification of the HCMV late structural protein pp65, improved methods of preventing and treating HCMV infection are needed. Introduction of CMV-specific CTL into a recipient is not a universally applicable and practical strategy to confer immunity to all those at-risk individuals who may need to be immunized against HCMV infection.

SUMMARY OF THE INVENTION

Accordingly, one aspect of the present invention relates to immunologically active peptides, and functional variants thereof, capable of eliciting a cellular immune response to HCMV in humans. The peptides are capable of directing human CTL to recognize and lyse human cells infected with HCMV. Such immunologically active peptides, in association with an MHC Class I molecule, are recognized by CTLs of individuals having a latent (inactive) HCMV infection.

Another aspect of the present invention provides a method of augmenting the immune system of a patient in need thereof (i.e., a patient harboring a latent or active CMV infection) by administering at least one immunologically active peptide according to the present invention that will be recognized by CTLs and/or CTLps (CTL precursors) of the patient.

In yet another aspect of the invention, at least one immunologically active peptide is administered to uninfected individuals to provide immunity against future infections by HCMV. Such a peptide may be administered in the form of a peptide or lipopeptide vaccine, optionally with an adjuvant.

Alternatively, the peptide(s) may be administered in the form of a cellular vaccine via the administration of autologous or allogeneic antigen presenting cells or dendritic cells that have been treated in vitro so as to present the peptide on their surface.

Yet another aspect of the invention is a method to augment the immune response of an individual who is latently infected with CMV and is at risk for reactivation of CMV infection, wherein T cells are removed from an individual and treated in vitro with a peptide of the present invention. The resulting CMV-reactive CTL are reinfused autologously to the patient or allogeneically to, for example, a BMT recipient.

In yet another aspect, a method to confer immunity against an HCMV infection to a previously uninfected individual includes the steps of removing T cells from the individual, exposing the T cells in vitro to a peptide of the present invention and then reinfusing the resulting HCMV-reactive CTL to the individual.

The peptides of the present invention also may be administered to previously infected or uninfected patients, or in vitro to T cells, in the form of a polynucleotide (DNA-based) vaccine, wherein a suitable gene transfer vector, such as a plasmid or an engineered viral vector that contains DNA encoding the peptide fragment under the control of appropriate expression regulatory sequences, is administered to the patient or to T cells in culture.

In yet another of its aspects, the present invention provides a vaccinia, canarypox or other eukaryotic virus vector containing a DNA sequence encoding the immunologically active peptide fragment. The vector infects an antigen presenting cell which in turn presents antigen that will be recognized by CTLs of patients having a latent (inactive) HCMV infection.

An additional aspect of the invention relates to diagnostic reagents for detection of the presence of active versus quiescent HCMV infections. The peptides according to the present invention can directly stimulate CTLp in vitro and therefore can be used in an assay to determine the degree of immunostimulation being caused by HCMV. The peptides can also be used to distinguish individuals who are seropositive from those who have not been exposed to HCMV (seronegative individuals). T cells from a patient can be contacted in vitro with APC that have been primed with a peptide according to the present invention.

DETAILED DESCRIPTION OF THE PREFERRED EMBODIMENTS

Figure 1:
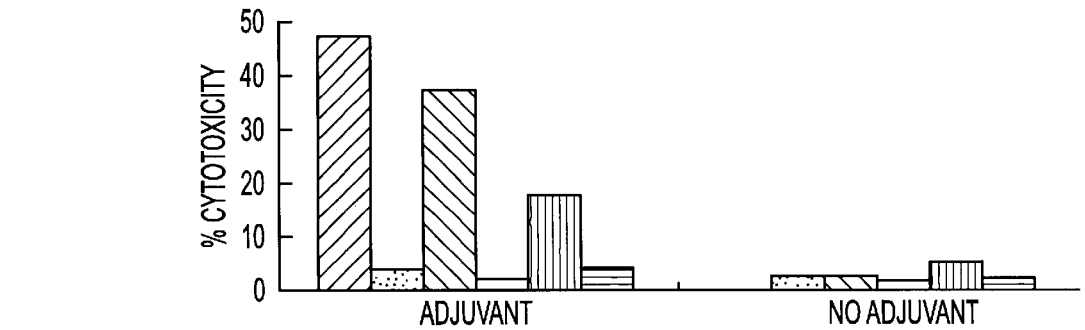
FIG. 1 shows the cytotoxic response elicited by peptides in the absence of lipidation.

According to one aspect of the present invention, a nonapeptide (9 amino acid peptide) of the sequence NLVPMVATV (pp65$_{495-503}$) (SEQ ID NO:1) is an immunogenic epitope of pp65 from CMV laboratory strains AD169 and Towne and all wild type isolates examined to date which is recognized by CD8+ Class I MHC restricted cytotoxic T-lymphocytes of patients harboring latent CMV infection. The peptide is capable of activating CTLs in the absence of active viral replication, and thus is useful for augmenting the immune system of normal and immunodeficient patients, as well as in the study of the Class I antigen processing pathway for HCMV proteins. The nonapeptide has amino acid residues in positions 2 and 9 which are the preferred residues at those positions for interaction with the HLA A*0201 and certain subtypes of HLA A*02XX, where XX=subtypes 02–22 (J. W. Drijfhout et al., *Human Immunology* 43:1–12 (1995)). Nonetheless, other less preferred amino acid residues may replace the preferred anchors, whereupon the peptide can continue to exhibit the capacity to bind HLA A*0201 and certain subtypes of HLA A*02XX with the ability to stimulate HCMV-specific CD8+ CTL.

Thus, in one aspect, the present invention provides an immunologically active peptide, capable of eliciting a cellular immune response to human cytomegalovirus infection, of the preferred sequence:

NLVPMVATV (SEQ ID NO:1).

Sequence variants of the preferred peptide include peptides of the sequence NX$_1$VPMVATX$_2$ wherein X$_1$ is L,I,M,T or V, and X$_2$ is V,A,C,I,L or T (SEQ ID NO:2). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

Other immunologically active peptides according to the present invention include the peptides:

YSEHPTFTSQY (SEQ ID NO:3)
which binds to HLA A*01XX including A*0101 and subtypes thereof. Sequence variants of this peptide include peptides of the sequence YXEHPTFTSQY wherein X is S, T or L (SEQ ID NO:4). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

FVFPTKDVALR (SEQ ID NO:5)
which binds to HLA A*68XX including A*6801 and subtypes thereof. Sequence variants of this peptide include peptides of the sequence FX$_1$FPTKDVALX$_2$ wherein X$_1$ is V or T and X$_2$ is L, R or K (SEQ ID NO:6). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

TPRVTGGGAM (SEQ ID NO:7)
which binds to HLA B*07XX including B*0702 and subtypes thereof. Sequence variants of this peptide include peptides of the sequence TPRVTGGGAX wherein X is L, F, or M (SEQ ID NO:8). The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

FPTKDVAL (SEQ ID NO:9)
which binds to HLA B*35XX including B*3502, B*3504, B*3506 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

RPHERNGFTVL (SEQ ID NO:19)
which binds to HLA B*07XX including B*0702 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

SVLGPISGHVLK (SEQ ID NO:20)
which binds to HLA A*11XX including A*1101 and other subtypes thereof with compatible peptide binding sites. The invention includes the construction and selection of other functional sequence variants, which can be carried out by those skilled in the art based upon the present disclosure. The peptide or the structural variants disclosed herein also can be a functional part of a longer peptide which produces the immunological effects disclosed herein.

EXAMPLE 1

Derivation of T-cell Clones

Methods for deriving T-cell clones from CMV seropositive individuals have been described in the literature (see above references). Forty to fifty milliliter samples of whole peripheral blood were obtained from CMV seropositive volunteers (detected by standard antibody methods). The white blood cells. (WBCs) were separated using Ficoll-HyPaque (DuPont) density gradient centrifugation. The whole blood was first centrifuged for 10 minutes at 1400 rpm in a tabletop centrifuge to reduce the number of red blood cells. The buffy coat was diluted to 12 ml with phosphate buffered saline (PBS), and 6 ml were layered on top of ½ volume of Ficoll-HyPaque. The top layer was removed after centrifugation at 2000 rpm in a tabletop centrifuge for 15–30 minutes. The interface containing the WBC was removed, diluted in PBS and recentrifuged for 8–12 minutes at 1000 rpm, which caused the WBC to pellet. The cells were again resuspended in PBS and washed as above one additional time. Four to five million WBC/ml were resuspended in T cell medium (TCM) with human serum obtained from pooled AB+ (blood group) CMV seronegative donors (HAB).

EXAMPLE 2

Derivation of LCL Antigen-Presenting Cells

Simultaneously, an autologous antigen presenting cell line was prepared by Epstein Barr virus immortalization of PBL (see Current Protocols in Immunology, Unit 7.22, Wiley-Liss Press (1993)). Deriving the CTLs and antigen presenting cells from the same individual ensures HLA matching between the cell lines.

EXAMPLE 3

In vitro Stimulation by HCMV

To initiate the in vitro stimulation of the WBC, a monolayer of autologous dermal fibroblasts obtained from the same volunteers as the WBC was established by plating the cells in 12-well plates at $10^5$ cells/ml/well in DMEM-10% HAB for 24 hours. After 24 hours in culture the fibroblasts were infected with CMV virions (AD169 or Towne strain) for 2 hours at a multiplicity of infection of between 1 and 5. The medium and virus were aspirated from the monolayer, and 1 ml of fresh DMEM-HAB was added. The monolayer was incubated in the medium for an additional 4 hours, following which time, the medium was aspirated. Two milliliters of medium containing 8–10 million WBCs were added per well containing CMV infected fibroblasts. The WBCs and fibroblasts were cultured in RPMI-1640 (Irvine Scientific) containing 50 U/ml penicillin, 50 µg/ml streptomycin, 4 mM L-glutamine, 25 µM 2-mercaptoethanol, 10 mM HEPES and 10% HAB (TCM-HAB). This was termed the first stimulation, and the cells were co-incubated for 7 days. TCM-HAB may be replaced if it becomes spent, or the culture may be expanded if there is vigorous cell growth.

The WBCs were re-stimulated on day 7 by plating onto a fresh monolayer of CMV-infected autologous fibroblasts prepared as described above. In addition, γ-irradiated (2500 rad) autologous PBL (5-fold over WBC) were added as feeder cells, and the medium was supplemented with recombinant IL-2 (10 IU/ml, Chiron-Cetus) on days 2 and 4 of this second stimulation. Wells which exhibit rapid cell growth require new medium containing IL-2 as the medium becomes spent.

After 12–16 days in culture, the cells were harvested and assayed for recognition of CMV matrix proteins in a chromium release assay (CRA). The CRA was performed by preparing APCs as target cells which are autologous or HLA-mismatched to the T-cell clone by infection with recombinant vaccinia viruses containing the DNA for HCMV proteins such as pp28 (pp28vac), pp65 (pp65vac) and pp150 (pp150vac) or wild-type virus strain WR.

After overnight infection, the APCs were incubated with chromium-51, and the assay was carried out as described (Current Protocols in Immunology, Wiley-Liss Press, Unit 7.17, (1993)). In the CRA, the vaccinia-infected APC (target cells) were loaded with chromium-51 and then mixed with cells from the T-cell clone (effector cells). Preferably, the cells are mixed at a series of effector: target cell ratios varying, for example from 20:1 to 1:1. After a 4 hour incubation period, the medium in which the cells were incubated was harvested. The release of radioactivity into the medium ($R_e$) was quantitated with a gamma scintillation counter. The extent to which infected antigen presenting cells exhibit spontaneous lysis and the release of radioactivity ($R_s$) in the absence of CTLs was established for each virus vector. The maximum amount of radioactivity incorporated into and releasable by the target cells ($R_{max}$) was established by lysis of target cells in a detergent (1% Triton X100; Sigma) solution. Percentage cytotoxicity can be expressed as:

$100 \times ((R_e) - (R_s))/((R_{max}) - (R_s))$.

Assays were deemed unacceptable and were repeated unless spontaneous release ($R_s$) was less than 30%.

Analysis of the assay was as described, with a positive result indicated by specific recognition of pp65vac infected autologous APC. A positive result for pp65 indicates that, in the tested polyclonal population, there are T cells which recognize the pp65 HCMV protein expressed by the virus.

EXAMPLE 4

Procedure for Identification of the CTL Epitope

WBC stimulated two times by HCMV on dermal fibroblasts were cloned by limiting dilution in 96 well U-bottom plates as follows. After 2 HCMV stimulations, the WBC were depleted of CD4$^+$ T cells by incubation with paramagnetic beads conjugated to anti-CD4 antibodies by negative selection. The resulting population was generally between 90–95% CD8$^+$, a reliable T cell subset marker, and generally 99% CD3$^+$, a marker for most peripheral blood T cells as assayed by either flow cytometry or fluorescence microscopy. This final population was plated at a concentration between 0.3–3 cells per well in a final volume of 150 µl. Each well also contained γ-irradiated 1.0–3.0×10$^5$ allogeneic peripheral blood mononuclear cells (PBMC) in TCM-HAB supplemented with 50–100 IU/ml recombinant IL-2 (Chiron-Cetus) and 0.5 µg/ml PHA (Murex).

After 3 days of culture, the PHA was diluted 2-fold by exchanging 75 µl with fresh culture medium supplemented with rIL-2. The wells were supplemented with fresh rIL-2 every 3–4 days, and medium was replaced as necessary. The cells were restimulated at between 12–14 days with fresh allogeneic PBMC as described above, and the plates were carefully observed for growth in individual wells. Visible cell growth indicates the need to transfer the expanding T cells to larger wells. T cells were restimulated every two weeks, and were transferred to progressively larger wells. At the stage of accumulation of several million cells, some were cryopreserved, and others were subjected to a further CRA. In this CRA, the targets were CMV infected fibroblasts, uninfected fibroblasts, autologous LCL infected with wild type vaccinia or vaccinia virus expressing either pp28, pp65 or pp150. HLA mismatched fibroblasts and LCLs were used as controls. One T cell clone among several tested, which was designated 3-3F4, had the characteristics of being both CMV and pp65-specific, and was reactive only to autologous targets in a specific manner. Other T cell clones with different HLA phenotypes were initially isolated in the same way, except that the initial peripheral blood sample came from different volunteers.

The HLA element which restricted the recognition of the T cell clone 3-3F4 to pp65 was identified. A series of LCL were used as targets that were singly autologous with each HLA allele of the 3-3F4 cell line. Each target was separately infected with pp65vac, wild type vaccinia, or not infected at all. The results showed that only the LCL that were autologous to the HLA A*0201 allele were being recognized and killed by the 3-3F4 T cell line. It was also established that 3-3F4 is of the CD8$^+$ T cell subset, characteristic of CTL which recognize Class I restricted peptides. Whether the cell line was monoclonal was tested by carrying out PCR repertoire analysis using a series of 26 human Vβ gene segment primers. Only one of 26 primers gave a significant signal, the Vβ13.1 primer, thereby demonstrating the apparent monoclonality of the 3-3F4 T cell clone.

To identify the precise epitope or peptide recognized by the T cell clone 3-3F4, a series of vaccinia truncations that deleted the pp65 protein from the carboxyl towards the amino terminus was used. A CRA utilizing autologous and HLA mismatched LCL as targets, infected with vaccinia viruses expressing truncation products of the pp65 protein, was conducted. This experiment localized a region between amino acids 377 and 561 that was necessary for killing of targets. Utilizing a small subset of amino terminal deletions, the region necessary for killing was further localized between amino acids 477 and 561. Utilizing an indirect killing assay, a monkey kidney cell line was transfected with the molecular HLA allele HLA A*0201 and portions of the pp65 gene to localize the region to a fragment containing amino acids 452–561. The final determination of the peptide sequence that corresponds to the sequence bound by HLA A*0201, and is recognized by T cell clone 3-3F4 was done by producing 9–10 amino acid peptides on the Synergy (Applied Biosystems Model 432) peptide synthesis machine. Using published information, a series of candidate sequences were determined that had significant characteristics of an HLA A*0201 binding sequence, and were located in the region between amino acid 452–561. These are:

TABLE 1

| Amino Acid Sequence of Peptide | Position Number | Motif | Score* |
|---|---|---|---|
| ILARNLVPMV (SEQ ID NO: 10) | 491 | A*0201 | 67 |
| ELEGVWQPA (SEQ ID NO: 11) | 526 | A*0201 | 59 |
| RIFAELEGV (SEQ ID NO: 12) | 522 | A*0201 | 55 |
| NLVPMVATV (SEQ ID NO: 1) | 495 | A*0201 | 63 |

*(adapted from J. D'Amaro et al., "A computer program for predicting possible cytotoxic epitopes based on HLA Class I peptide binding motifs," Human Immunology 43:13–18 (1995)).

Only one of these peptides (referred to as "the 495 peptide" or as "pp65$_{495-503}$") (SEQ ID NO:1) proved capable of priming the autologous LCL to be recognized and killed by the CD8$^+$ CTL 3-3F4. Other 9–10 amino acid peptides from pp65 that also followed the HLA A*0201 motif were tested in the CRA. None showed any activity. All peptides were examined by HPLC on a Vydac C$_{18}$ column using acetonitrile/TFA as the moving phase. They were 70–80% pure or greater on average, and were used as dilutions from 0.1% acetic acid solution.

EXAMPLE 5

Use of the 495 Peptide To Induce Cell Lysis

Serial dilutions of the 495 peptide showed no change in activity between 10 μM and 0.01 μM in priming the autologous LCL for killing by T cell clone 3-3F4 in a CRA. Half-maximal lysis occurred at close to 0.5 nM peptide. The peptide-transporter deficient cell line T2 (D. B. Crumpacker et al., *J. Immunol.* 148:3004–3011 (1992)), which is HLA A*0201 positive, also was used to test the lower limits of sensitivity of the 3-3F4 T cell clone for recognition of the peptide in a CRA. It was found that as little as 0.1 nM peptide caused maximal lysis of T2 cells, equivalent to the condition with 10 nM peptide. These experiments demonstrate that this minimal cytotoxic epitope is a strong binder to the HLA A*0201 allele.

The 495 peptide depicted in Table 1 was prepared on a Synergy (Applied Biosystems Model 432) peptide synthesis machine. Dermal fibroblasts were primed with the peptide, then loaded with chromium-51 via the following procedure. Dermal fibroblasts were incubated with 10 μM of the 495 peptide for 2 hours at 37° C., and for the final hour with chromium-51. The peptide and chromium-51 were washed out of the medium.

T cell clone 3-3F4 (CD8$^+$ CTL) derived from an HCMV seropositive individual (HLA A*0201 positive) as described above was capable of recognizing the HCMV-infected fibroblasts as well as the peptide-primed fibroblasts in a CRA. Uninfected and unprimed fibroblasts were not recognized or killed by the T cell clone. In addition, an HLA-mismatched fibroblast line without the HLA A*0201 allele found on the donor fibroblasts was not recognized or killed by the T cell clone when it was either infected by HCMV or primed with the 495 peptide. Thus, the 495 peptide of the present invention can serve as a "substitute" for the whole HCMV virus in causing normal T cells to recognize and kill fibroblasts as effectively or better than if they were infected with HCMV.

EXAMPLE 6

Generation of TNF-α by T Cell Clones

TNE-α is a T cell lymphokine that is cytotoxic for many cell types and may contribute to the in vivo immune response mounted against an HCMV infection. Cells of the 3-3F4 T cell clone were incubated with autologous fibroblasts pre-incubated with either whole HCMV virions or primed with the 495 peptide of Table 1. Twenty four hours later, supernatants from the co-incubated cells were applied to an indicator cell line in a bioassay as described above. The indicator cell line, a WEHI derivative, is sensitive to the cytotoxic action of TNF-α down to the picomolar level.

Peptide-primed fibroblasts induced the production of as great or greater levels of TNF-α from T cell clone 3-3F4 as were the HCMV-infected fibroblasts. The inventive 495 peptide did not induce TNF-α production by either autologous fibroblasts incubated without T cells or non-HLA-A*0201 expressing fibroblasts incubated with the T cell clone.

EXAMPLE 7

495 Peptide Can Induce CTL from PBL of HCMV Seropositive Individuals

PBL from HCMV-seropositive individuals were plated onto 495 peptide-primed autologous fibroblasts for 7 days. The once-stimulated PBL were re-stimulated in a similar manner, either with or without depletion of CD4 T cells. After two weeks, a CRA was performed using as targets either peptide-primed, CMV-infected, or untreated autologous fibroblasts. CD8$^+$ CT cells lysed significant percentages of the peptide primed and CMV infected fibroblasts, but not untreated cells. No autologous fibroblast targets were lysed by CD4-depleted PBL from freshly drawn blood under the same conditions.

EXAMPLE 8

Human Cell Lines Which Express HLA A2, With Molecular Subtypes Other Than A*0201, Are Sensitized to Lysis by The 495 Peptide Twelve cell lines were subjected to CRA in which they were pulsed with the 495 peptide (pp65$_{495-503}$) nonamer, loaded with chromium-51, and incubated with two different HLA A*0201 restricted CTL which recognize the 495 peptide and HCMV. The specific cytotoxicity was calculated and is shown in tabular form below for the 1 μM and 1 nM concentrations of the 495 peptide. A plus sign (+) represents cytotoxicity greater than 30%, a plus/minus sign (+/−) represents cytotoxicity between 15% and 30%, and a minus sign (−) represents cytotoxicity less than 15%.

TABLE 2

| | CTL 3-3F4 | | CTL VB-57 | |
|---|---|---|---|---|
| HLA A2 Subtype | 1 μM | 1 nM | 1 μM | 1 nM |
| A*0201 | + | + | + | + |
| A*0202 | + | − | + | − |
| A*0203 | + | − | − | − |
| A*0204 | + | + | + | + |
| A*0205 | + | − | + | + |
| A*0206 | + | + | + | + |
| A*0207 | + | + | + | + |
| A*0209 | + | − | + | − |

TABLE 2-continued

| HLA A2 Subtype | CTL 3-3F4 | | CTL VB-57 | |
| --- | --- | --- | --- | --- |
| | 1 μM | 1 nM | 1 μM | 1 nM |
| A*0210 | + | + | + | + |
| A*0211 | + | − | + | − |
| A*0217 | + | − | + | + |

The data show that all tested subtypes functionally bind the 495 peptide at 1 μM, and the cell lines are lysed by the HCMV and pp65 specific CTL. This data shows that the cell line subtypes shown here are capable of being sensitized for lysis by the 495 peptide. The data also indicate that cells from individuals who carry these subtypes can be sensitized by the peptide for CTL recognition and lysis, albeit at a higher concentration in most cases than what was found for HLA A*0201. Thus, individuals who carry any of these HLA A2 subtypes may respond to the 495 peptide as a vaccine.

EXAMPLE 9

Animal Studies Using The 495 Peptide (SEQ ID NO:1)

A transgenic mouse model, the HLA A2.1 mouse (E. J. Bernhard et al., *J. Exp. Med.* 168:1157–1162 (1988)), was employed to test whether the 495 peptide could stimulate CTLs lacking prior virus exposure and function as a vaccine. Three mice were immunized subcutaneously at the base of the tail with 50 μg of the 495 peptide ($pp65_{495-503}$) or peptide $p53_{149-157}$ from p53 (M. Theobald et al., *Proc. Natl. Acad. Sci. U.S.A.* 92:11993–11997 (1995)) together with 20 μg of the polyclonal helper T lymphocyte (HTL) peptide (PADRE) (J. Alexander et al., *Immunity.* 1:751–761 (1994)) emulsified in IFA (Incomplete Freund's Adjuvant). After twelve days, spleens were removed from immunized mice, a splenic suspension was made, and the effector cells were restimulated for one week using $P53_{149-157}$ or $pp65_{495-503}$ peptide sensitized syngeneic lipopolysaccharide-treated splenic blast cells (P. A. Wentworth et al., *Eur. J. Immunol.* 26:97–101 (1996)). Thereafter, for subsequent in vitro stimulations, the stimulator cells were Jurkat A2.1 cells, prepared by acid treatment and subsequent loading of peptides (Z. Yu et al., *Journal of Surgical Research* 69:337–343 (1997)). After two in vitro restimulation cycles, the murine splenic effector population was tested for recognition of $p53_{149-157}$ or $pp65_{495-503}$ peptide loaded T2 cells. There was substantial recognition of $pp65_{495-503}$ or $p53_{149-157}$ peptide in mice that had been appropriately immunized, without recognition of the non-immunizing peptide.

It was also demonstrated that murine splenic effectors recognize endogenously processed pp65 in a CRA with human HLA A*0201 EBVLCL targets infected with pp65Vac (D. J. Diamond et al., *Blood* 90 (5):1751–1767 (1997)). Further proof that the $pp65_{495-503}$ peptide causes recognition of virus-infected cells came from a CRA using HCMV-infected human fibroblasts as targets, and murine CTL derived from the $pp65_{495-503}$ peptide stimulation as the effector population. HLA A*0201 fibroblasts infected with HCMV were capable of lysis by the CTL, whereas both uninfected and mismatched fibroblasts were not recognized (D. J. Diamond et al. *Blood* 90 (5):1751–1767 (1997)). Taken together, these results clearly show that the splenic effector population from a primary immunization with $pp65_{495-503}$ are recognizing endogenously processed pp65 and HCMV in an HLA A*0201 restricted manner.

An additional study demonstrated that the 495 peptide can induce a long-lived immune response in animals. Twelve mice were simultaneously immunized with the 495 peptide+PADRE+IFA, and two additional mice were immunized with HTL+IFA alone. At two weeks, 6 weeks, 10 weeks and 14 weeks after the immunization, the spleens from two immunized mice were analyzed for immunity against the 495 peptide or a control peptide from human p53 ($P53_{149-157}$). In addition, at two and six weeks, mice immunized without the 495 peptide were also sacrificed and their spleen cells analyzed for immune responses against the 495 peptide or the human p53 peptide. Percent specific cytotoxicity (cytotoxicity of 495 peptide targets—cytotoxicity of p53 targets) was still at a level of 40% after 14 weeks, whereas naive animals did not show any specific cytotoxicity above 5%. This compared well with recent results from immunizing human volunteers with the Theradigm™ lipopeptide (B. Livingston et al., *J. Immunol.* 159:1383–1392 (1997)) in which there was an average maintenance of 60% of the initial response 38 weeks after the final of four immunizations over an eighteen week period.

EXAMPLE 10

Lipidated Peptides Incorporating $pp65_{495503}$ (SEQ ID NO:1) as IFA-Adjuvant Independent Vaccines in Animals Although the use of adjuvants to enhance immunogenicity is a common strategy in animal studies, there are important limitations concerning their use in humans. To avoid having to use adjuvants, peptides which incorporate lipid molecules were prepared. This strategy has been efficacious in both animal (K. Deres et al., *Nature* 342:561–564 (1989)) and human clinical studies (A. Vitiello et al., *J. Clin. Invest.* 95:341–349 (1995)).

Either one or two palmitic acid moieties were attached to the amino terminus of the 495 peptide, and a series of immunization studies was conducted in the transgenic HLA A2.1 mouse. The primary structure of the directly lipidated peptides is shown in Table 3.

TABLE 3

Primary Structure of Peptides Used to Immunize HLA A2.1 Transgenic Mice

| Lipid Molecule(s) | Adapter Sequence | Epitope Sequence (SEQ ID NO: 1) | Carboxyl Terminus |
| --- | --- | --- | --- |
| 0 | -KSS- | -NLVPMVATV- | OH |
| 1 PALMITIC ACID | -KSS- | -NLVPMVATV- | OH |
| 2 PALMITIC ACID | -KSS- | -NLVPMVATV- | OH |

Table 3. Peptides were synthesized on the ABI 432 (Applied Biosystems), and purified and analyzed as described (D. J. Diamond et al., *Blood* 90 (5):1751–1767 (1997)). Palmitic acid (Aldrich) was dissolved in dimethylformamide, and automatically coupled to the amino terminal lysine. The amino terminal lysine of the monolipidated form of the peptide was protected by two protecting groups, Fmoc and Boc. Only the Fmoc group is cleaved during synthesis to allow for a single lipid moiety to be added. For the dilipidated form, the amino terminal lysine was protected with two Fmoc groups, therefore allowing two lipid moieties to be added. Peptides also may be lipidated at other locations by methods well known in the art.

Figure 2:
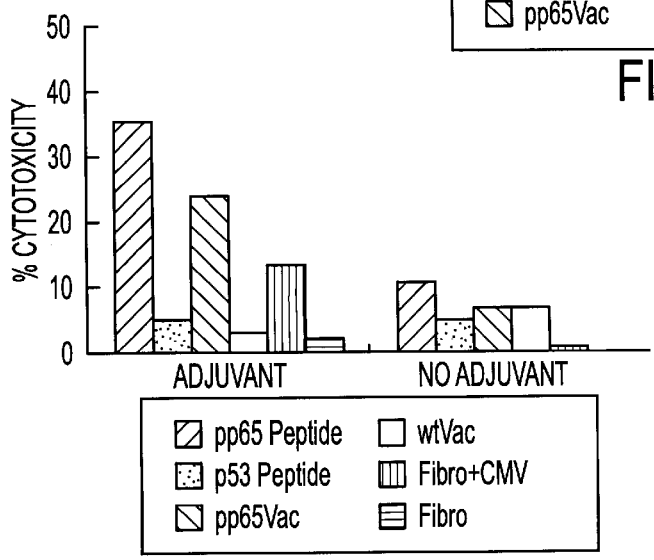
FIG. 2 shows the cytotoxic response elicited by mono-lipidated peptides.
Figure 3:
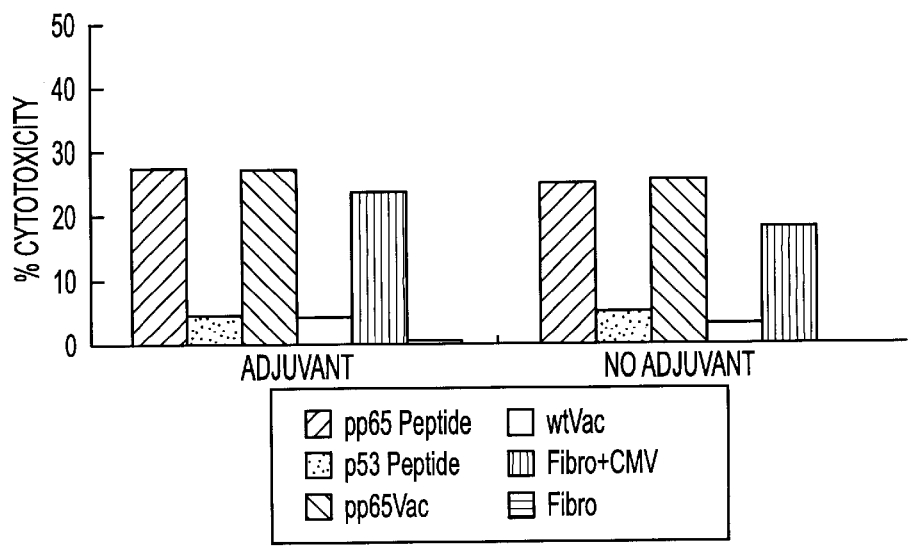
FIG. 3 shows the cytotoxic response elicited by dilapidated peptides.

Separate mice were immunized with unmodified $pp65_{495-503}$, and either the monolipidated or dilipidated forms of the peptide together with the PADRE epitope. Because it has been previously shown that lipidated peptides will stimulate immunity without co-administration of Freund's adjuvant (H. Schild et al., *Eur. J. Immunol.* 21:2649–2654 (1991)), immunization of mice with and without emulsifying the peptides in IFA was compared. In a procedure similar to the procedure described in Example 9 above, twelve days post inoculation the mice were splenectomized and the spleen cell population was restimulated twice in vitro. The splenic effectors were then tested in a CRA with peptide-loaded T2 cells, EBVLCL targets infected with pp65Vac, and HCMV-infected fibroblasts (D. J. Diamond et al., *Blood* 90 (5):1751–1767 (1997)). The results demonstrate that the lipidated form of the 495 peptide, without emulsification in adjuvant, induces an immune response capable of recognizing endogenously-processed pp65 and HCMV-infected human cells. The monolipidated form appeared to induce a weaker immune response (compare with and without IFA), whereas the unmodified free peptide had no activity unless emulsified in IFA. (See FIGS. 1–3)

These data illustrate an advantageous immunization/vaccination procedure for use in warm blooded animals including humans. The procedure entails the mixture of two peptides in an aqueous solvent system (the lipidated 495 peptide plus either PADRE or the 830–843 amino acid tetanus peptide, Table 3). The mixture is administered subcutaneously or via another acceptable and efficacious route to either HCMV seropositive or seronegative subjects. An additional set of booster injections may be employed to enhance the immunity induced by primary vaccination.

EXAMPLE 11

Formulation of Lipidated Vaccines

The 495 peptide and functional sequence variants thereof can be formulated as a vaccine as a lipidated peptide with a covalent HTL epitope. The HTL epitope can be any peptide that has broad reactivity to human MHC class II to stimulate a classic helper response. Such molecules include but are not limited to amino acids 830–843 from tetanus toxin (P. Panina-Bordignon et al., *Eur. J. Immun.* 19:2237–2242 (1989)), HTL epitopes from HIV envelope protein (J. A. Berzofsky et al., *J. Clin. Invest.* 88:876–884 (1991)), or a synthetic version (PADRE) predicted from known anchor residues (J. Alexander et al., *Immunity* 1:751–761 (1994)).

The lipidation of the HTL+CTL epitope preferably is performed on the amino terminus of the HTL epitope, with the HTL epitope being amino terminal to the CTL epitope. Suitable lipid moieties are known and described in the literature. (H. Schild et al., *Eur. J. Immunol.* 21:2649–2654 (1991); A. Vitiello et al., *J. Clin. Invest.* 95:341–349 (1995); K. Deres et al., *Nature* 342:561–564 (1989)). Alternatively, the CTL epitope can be lipidated at its amino terminus, followed by the HTL epitope, or the lipid can be found at the carboxyl terminus followed by either the CTL or HTL epitope(s). A three amino acid spacer can be inserted between the HTL and CTL epitope, or the epitopes can be fused directly in frame. Alternatively the CTL epitope lipidated on its amino terminus can be administered together with the HTL epitope, without covalent attachment. The vaccine epitopes, regardless of primary structure, may be injected s.c. into the forearm in a standard formulation buffer (PBS/10% DMSO or higher concentration/0.01% triflouroacetic acid or other acid or alcohol of the same or different concentration) once. Three to six weeks later, a booster injection of the same material may be administered. Multiple booster injections spaced three to six weeks apart can be subsequently administered, if necessary.

This injection series can be administered to a patient or at-risk individual, or to the donor of a bone marrow transplant, who is either positive or negative for the virus. Illustrative examples of lipidated vaccine peptides include:

TABLE 4

| N-terminal | C-terminal |
|---|---|
| (Pam)$_2$-KSS*QYIKANSKFIGITE*<u>AAA</u>NLVPMVATV | (SEQ ID NO:13) |
| (Pam)$_3$-CSS*QYIKANSKFIGITE*<u>AAA</u>NLVPMVATV | (SEQ ID NO:14) |
| (Pam)$_2$-KSS*AKXVAAWTLKAAA*<u>GGG</u>NLVPMVATV | (SEQ ID NO:15) |
| (Pam)$_3$-CSS*AKXVAAWTLKAAA*<u>GGG</u>NLVPMVATV | (SEQ ID NO:16) | wherein X is cyclohexylalanine or phenylalanine. As is the case throughout, all amino acids are represented by their universal one-letter code. "Pam" is palmitic acid. The three-A or -G spacer (underlined) can be interchanged among vaccine peptides. The format of the peptides shown above can be described (from the amino terminus) as: lipid-K/CSS—HTL epitope (italics)—amino acid spacer (underlined)—CTL epitope. The positions of the CTL and HTL epitopes may be interchanged. The CTL epitope (or a functional sequence variant thereof) may be further modified by adding a leader sequence and/or the amino acids KDEL can be appended to the carboxyl terminus for retention and targeting into the endoplasmic reticulum. Palmitic acid or any suitable lipid may be used, including but not limited to stearic acid, myristic acid, lauric acid, capric acid and decanoic acid.

EXAMPLE 12

Use of Combined HTL and CTL Epitope, Lipidated at the Amino Terminus, as a Single Component Vaccine in Transgenic Mouse Studies Two further molecules, each containing lipid, HTL and CTL epitopes, were constructed and tested in mice:

TABLE 5

| N-terminal | C-terminal |
|---|---|
| A. (Pam)2-KSS*AKXVAAWTLKAAA*NLVPMVATV | (SEQ ID NO:17) |
| B. (Pam)2-i KSS*ISQAVHAAHAEINE* <u>AAA</u>NLVPMVATV | (SEQ ID NO:18) |

Nomenclature for Table 5 can be found in the legend to Table 4.

Molecule A (SEQ ID NO:17) is a vaccine that has the capability of working in mice and humans, whereas molecule B (SEQ ID NO:18) should only be functional in mice. One hundred nanomoles of each of these vaccine peptides in 25% dimethysulfoxide in phosphate buffered saline with 2.5% hexafluoroisopropanol were injected s.c. into separate transgenic HLA A2.1 mice.

The methods referred to in Examples 9 and 10 were used to derive spleen cell populations containing cells which were specific against pp65 and HCMV. The spleen cells from immunized mice were tested for recognition and cytolysis against specific and non-specific peptide-sensitized targets, HCMV infected and non-infected HLA A*0201 and HLA-mismatched fibroblast targets. The 495 $\mu$p65$_{495\text{-}503}$ peptide sensitized targets were effectively lysed, whereas targets sensitized with a peptide derived from another protein (human p53) which binds to HLA A*0201 (p53$_{149\text{-}157}$) were ineffective. In addition, and importantly, HCMV-infected HLA A*0201 fibroblasts were effectively lysed, but uninfected fibroblasts or those which are HLA-mismatched were not recognized or lysed, regardless of HCMV infection. These results were obtained with both molecules A and B, although molecule A was the more potent of the two. However, a second immunization (booster) of mice immunized with Vaccine A at lesser amounts of 50 nmole resulted in a detectable immune response when a single immunization was not effective (Table 5). This stimulative effect of the booster is in agreement with B. Livingston et al., *J. Immunol.* 159:1383–1392 (1997)). These data show that the single molecule form of the vaccine functions to stimulate HCMV immunity in an animal model without any added molecules or adjuvant other than the vaccine molecules A or B (Table 4)in liquid vehicle (PBS/DMSO/HFIP). The data also demonstrate that the vaccine is capable of stimulating a de novo immune response to HCMV in a HCMV-naive mouse.

EXAMPLE 14

Additional HCMV pp65 CTL Epitopes Specific for HLA A and B Alleles

The experimental design used to determine the sequence of the 495 peptide and its function is described in Examples 1–13. The 495 peptide specifically bound to HLA A*0201 and the other subtypes shown in Example 8.

There are over 100 known HLA Class I alleles of the A and B genes, however. (J. G. Bodmer et al., *Tissue Antigens* 49:297–321 (1997)). Using a combination of predictive algorithms and truncation analysis, additional peptides from pp65 that will sensitize both autologous and allogeneic cells to be lysed by MHC-restricted human CTL were identified. As discussed in Example 1, the CTL arise from HCMV seropositive humans; therefore, the defined epitopes from pp65 were those used by humans to suppress endogenous HCMV reactivation or viremia. To define CTL reactive against HCMV pp65 in combination with specific HLA alleles, individual cloned CTL lines were tested for recognition of EBVLCL infected with pp65vac which contained one of the HLA A or B alleles found in the individual whose blood was used to derive the CTL. In cases where at least one HLA allele is shared between the EBVLCL targets and the CTL, sensitization for recognition and lysis was observed. This experiment was repeated with at least three independent cell lines containing the restricting allele. Table 6 shows the pp65 epitopes, their HLA restriction, the number of independent cell lines of the same restriction which were sensitized, and the method(s) of delineation of the epitopes.

TABLE 6

| HLA A or B Allele Specificity | Number of Test Cell Lines | Method(s) of Determination | Minimal Cytotoxic Epitope Sequence |
| --- | --- | --- | --- |
| HLA A*0101 and subtypes | 3 | A, B, C, D, E | YSEHPTFTSQY (SEQ ID NO: 3) |
| HLA A*6801 and subtypes | 3 | A, B, D, E | FVFPTKDVALR (SEQ ID NO: 5) |
| HLA B7 and subtypes | 5 | A, B, D, E | TPRVTGGGAM (SEQ ID NO: 7) |
| HLA B*3502, 04, 06 and subtypes | 3 | A, B, C, D, E | FPTKDVAL (SEQ ID NO: 9) |
| HLA B7 and subtypes | 5 | A, B, C, E | RPHERNGFTVL (SEQ ID NO: 19) |

TABLE 6-continued

| HLA A or B Allele Specificity | Number of Test Cell Lines | Method(s) of Determination | Minimal Cytotoxic Epitope Sequence |
| --- | --- | --- | --- |
| HLA A*1101 and subtypes | 5 | A, B, C, E | SVLGPISGHVLK (SEQ ID NO: 20) |

Methods of Determination: (A) HLA Restriction using single HLA allele matched cell lines; (B) pp65 truncations in vaccinia viruses; (C) pp65 truncations in plasmids with detection of activity using TNF-α assay; (D) matching of amino acid residues using published motifs; (E) functional analysis using ordered overlapping peptides.

EXAMPLE 15

Vaccine Molecules Comprised Of More than One CTL Epitope

In accordance with the procedures described herein, vaccines containing a combination of pp150 and/or pp65 epitopes, specific for the same or different HLA Class I restriction elements, were prepared. For vaccination of humans there is no necessity for each epitope to have the same MHC restriction. A vaccine molecule which targets two or more MHC restriction elements may be preferred because it allows the production of fewer vaccine molecules, in a polymorphic population. Peptides with CTL epitopes which are restricted by frequently expressed HLA alleles (see Tables 1 and 6) are preferred, and polypeptide vaccines containing epitopes from both the pp65 and pp150 proteins, as well as an HTL epitope, are especially preferred for human vaccination against HCMV. The HLA alleles shown in Tables 1 and 6 are a subset of possible HLA A,B, and C CTL epitopes to be potentially included in a multiple CTL epitope vaccine molecule. The inclusion of multiple CTL epitopes and an HTL epitope will lengthen the peptides (in the range of 40–50 amino acids). Therefore, the hydrophobicity of the sequence is an important factor. Alternatively, HCMV polypeptide vaccines may be prepared without a covalently attached HTL epitope by using multiple CTL epitopes with a spacer of three alanine residues or another combination of amino acids between each epitope, and two palmitic acid-lysyl amides at the N-terminus, as shown in Table 3.

EXAMPLE 16

Immunization of BMT Patients

A therapeutically active form of an antigenic peptide according to the present invention may be administered to an HCMV-seropositive bone marrow transplant donor at a sufficient time (six to eight weeks, for example) in single or multiple doses separated by a given number of days or weeks prior to bone marrow transplant to enable the development of an anti-HCMV cellular immune response. The antigenic peptide can be formulated in per se known manners (for example, as a lipidated peptide, optionally in combination with a helper peptide and/or an adjuvant) and will be administered, preferably, in multiple doses. If an unmanipulated BMT graft will be given to the recipient, such a graft will contain 25% or more of mature T cells. The T cells will confer active immunity to the BMT recipient patient. Alternatively, when a T-cell depleted BMT graft is to be employed, an aliquot of T cells from the immunized donor can be administered to the patient following (for example, approximately 21 to 35 days) BMT in order to provide the recipient patient with HCMV immunity.

EXAMPLE 17

In Vitro Assay For HCMV Infected Cells

The peptides of the present invention may be used in an in vitro assay to detect the presence or absence of HCMV-infected cells obtained, for example, from a patient who's HCMV status (infected or uninfected) is unknown. T lymphocytes obtained from the patient are incubated with APC primed with a peptide of the present invention. The activation of CTLs or CTLp's will reveal that the patient was infected with HCMV.

Although certain preferred embodiments and examples of the invention have been described, the invention is not so limited. Persons skilled in this field of science will understand that the present invention is capable of wide application in the fields of diagnostics and therapeutics, and that modifications and variations can be made to the invention without departing from its spirit and scope.

We claim:
1. A peptide according to SEQ ID NO: 19.
2. A peptide according to SEQ ID NO: 20.
3. A vaccine against human cytomegalovirus comprising a peptide selected from SEQ ID NO: 1, SEQ ID NO: 19 and SEQ ID NO: 20.
4. A vaccine according to claim 3, wherein said peptide is lipidated.
5. A vaccine according to claim 4, wherein said peptide is monolipidated.
6. A vaccine according to claim 4, wherein said peptide is dilipidated.
7. A cellular vaccine against human cytomegalovirus comprising antigen presenting cells that have been treated in vitro so as to present a peptide according to claim 3.
8. A cellular vaccine according to claim 7, wherein said antigen presenting cells are autologous.
9. A cellular vaccine according to claim 7, wherein said antigen presenting cells are allogeneic.

* * * * *

UNITED STATES PATENT AND TRADEMARK OFFICE
CERTIFICATE OF CORRECTION

PATENT NO. : 6,251,399 B1
DATED : June 26, 2001
INVENTOR(S) : Don Jeffrey Diamond Page 1 of 1

It is certified that error appears in the above-identified patent and that said Letters Patent is hereby corrected as shown below:

Title page,
Insert Item:
-- [73]  Assignee: City of Hope, Duarte, CA (US) --
Item [76], Inventors, please delete "Joanne York, 40587 174$^{th}$ St. East, Lancaster, CA (US) 93535"

Column 13,
Line 7, "A*0211   +   -   +   -" should read -- A*0211   +   -   +   +/- --
Line 23, "SEO" should read -- SEQ --

Column 14,
Line 25, in the Title of Example 10, "pp65$_{495503}$" should read -- pp65$_{495-503}$ --

Column 16,
Line 46, Table 5, "(Pam) 2-i" should read as -- (Pam) 2- --

Signed and Sealed this

Seventeenth Day of August, 2004

JON W. DUDAS
*Acting Director of the United States Patent and Trademark Office*